US010849900B2

(12) United States Patent
Cade et al.

(10) Patent No.: US 10,849,900 B2
(45) Date of Patent: Dec. 1, 2020

(54) TREATMENT OF NEOPLASIA

(71) Applicant: SIRTEX MEDICAL LIMITED, North Sydney (AU)

(72) Inventors: David Cade, North Sydney (AU); Michael Tapner, North Sydney (AU)

(73) Assignee: Sirtex Medical Limited, North Sydney (AU)

( * ) Notice: Subject to any disclaimer, the term of this patent is extended or adjusted under 35 U.S.C. 154(b) by 218 days.

(21) Appl. No.: 15/114,058

(22) PCT Filed: Jan. 23, 2015

(86) PCT No.: PCT/AU2015/000037
§ 371 (c)(1),
(2) Date: Jul. 25, 2016

(87) PCT Pub. No.: WO2015/109367
PCT Pub. Date: Jul. 30, 2015

(65) Prior Publication Data
US 2017/0000795 A1    Jan. 5, 2017

(30) Foreign Application Priority Data
Jan. 24, 2014  (AU) ................................ 2014900232

(51) Int. Cl.
| *A61K 31/519* | (2006.01) |
| *A61K 31/513* | (2006.01) |
| *A61K 45/06* | (2006.01) |
| *C07K 16/22* | (2006.01) |
| *A61K 31/555* | (2006.01) |
| *A61K 31/282* | (2006.01) |
| *A61K 51/12* | (2006.01) |
| *A61K 41/00* | (2020.01) |
| *A61K 39/395* | (2006.01) |
| *A61N 5/10* | (2006.01) |
| *C07K 16/30* | (2006.01) |
| *A61K 39/00* | (2006.01) |

(52) U.S. Cl.
CPC .......... *A61K 31/519* (2013.01); *A61K 31/282* (2013.01); *A61K 31/513* (2013.01); *A61K 31/555* (2013.01); *A61K 39/3955* (2013.01); *A61K 41/0038* (2013.01); *A61K 45/06* (2013.01); *A61K 51/1244* (2013.01); *A61N 5/1001* (2013.01); *C07K 16/22* (2013.01); *C07K 16/30* (2013.01); *A61K 2039/505* (2013.01); *A61K 2039/545* (2013.01); *C07K 2317/24* (2013.01)

(58) Field of Classification Search
CPC .. A61K 31/519; A61K 31/282; A61K 31/513; A61K 39/395; A61K 45/06; C07K 16/22; C07K 16/30; A61N 5/10
See application file for complete search history.

(56) References Cited

FOREIGN PATENT DOCUMENTS

WO WO-2011034954 A1 * 3/2011 ........... C07D 491/22
WO WO 2005/002629 A1 1/2015

OTHER PUBLICATIONS

Over Gulec et al., Yttrium-90 Microsphere-selective Internal Radiation Therapy with Chemotherapy (Chemo-DIRT) for Colorectal Cancer liver Metastases; Am J Clin Oncol 2013;36:455-460.*
Yanmaz et al., Thirty-minutes infusion rate is safe enough for bevacizumab; no need for initial prolong infusion, Med Oncol (2014) 31:276.*
Al-Husein et al., Anti-angiogenic therapy for cancer: an update, Pharmacotherapy. Dec. 2012; 32(12): 1095-1111.*
Multiple authors; Colorectal Cancer, Annals of Oncology, Supplement 4 to vol. 11, 2000. (Year: 2000).*
Gkioulbasanis et al., Dose escalating clinical study of high dose infusional 5-fluorouracil and leukovorin (AIO regimen) plus alternate weekly administration of oxaliplatin and irinotecan in patients with advanced tumors of the gastrointestinal tract, Journal, (BUON 12: I 07-202, 2007. (Year: 2007).*
Gulec, S.A. "Yttrium-90 microsphere-selective internal radiation therapy with chemotherapy (chemo-SIRT) for colorectal cancer liver metastases: an in vivo doublearm-controlled phase II trial." Am J Clin Oncol. (Oct. 2013); 36 (5):455-460.
Sharma, R.A. et al. "Radioembolization of liver metastases from colo rectal cancer using yttrium-90 microspheres with concomitant systemic oxaliplatin, fluorouracil, and leucovorin chemotherapy." J Clin Oneal. (Mar. 20, 2007); 25 (9):1099-1106.
Vente, M. A. et al. "Yttrium-90 microsphere radioembolization for the treatment of liver malignancies: a structured meta-analysis." Eur Radio!. (Apr. 2009); 19( 4):951-959.
Kosmider, S. et al. "Radioembolization in combination with systemic chemotherapy as first-line therapy for liver metastases from colorectal cancer." J Vase Intery Radiol. (Jun. 2011); 22(6):780-786.
Sharma, R.A. et al. "FOXFIRE: a phase III clinical trial of chemo-radio-embolisation as first-line treatment of liver metastases in patients with colorectal cancer." Clin Oncol. (Apr. 2008); 20(3):261-263.
Hrehoret, D. et al. "Liver transplantation in a patient with unresectable colorectal liver metastases—a case report." Chirurgia. (Sep.-Oct. 2013); 1 08(5):719-724.
Gibbs, P. et al. "Selective Internal Radiation Therapy (SIRT) with yttrium-90 resin microspheres plus standard systemic chemotherapy regimen ofFOLFOX versus FOLFOX alone as first-line treatment of non-resectable liver metastases from colorectal cancer: the SIRFLOX study." BMC Cancer. (Dec. 1, 2014); 14:897.
Dutton, S.J. et al. "FOXFIRE protocol: an open-label, randomised, phase III trial of 5-fluorouracil, oxaliplatin and folinic acid (OxMdG) with or without interventional Selective Internal Radiation Therapy (SIRT) as first-line treatment for patients with unresectable liver-only or liver-dominant metastatic colorectal cancer." BMC Cancer. (Jul. 9, 2014); 14:497.

(Continued)

Primary Examiner — Robert A Wax
Assistant Examiner — Nabila G Ebrahim
(74) Attorney, Agent, or Firm — Stites & Harbison PLLC; Richard S. Myers, Jr.

(57) ABSTRACT

A method of treating cancer in a patient comprising administering to the patient an a systemic chemotherapeutic drug regime in combination with radioactively doped particle, characterised in that the two therapies when introduced into the patient have an improved anticancer effect.

18 Claims, No Drawings

(56) References Cited

OTHER PUBLICATIONS

Alberts Steven Red—Niesvizky DR Ruben: "Update on the optimal management of patients with colorectal liver metastases", Critical Reviews in Oncology/Hematology, vol. 84, No. 1, 2012, pp. 59-70.
Kara Nyberg: "SIRT offers no benefit when added to chemotherapy for mCRC with liver metastases", ASCO Daily News 1' Jun. 3, 2017 (Jun. 13, 2017), XP002772518, Retrieved from the Internet: URL:https://am.asco.org/sirt-offers-no-benefit-when-added-chemotherapy-mcrc-liver-metastases.
Anonymous: "FOLFOX plus SIR-spheres microspheres versus FOLFOX alone in patients with liver mets from primary colorectal cancer (SIRFLOX)", ClinicalTrials.gov—U.S. National Institutes of Health 7' Nov. 2013 (Nov. 7, 2013), XP002772519, Retrieved from the Internet: URL:https://web.archive.org/web/20131111074806/https://clinicaltrials.gov/ct2/show/NCT00724503.
Clinical trial NCT00724503. Sep. 30, 2013.
Sharma R. A., Synergy of yttrium-90 microspheres therapy with radiosensitising chemotherapy. EJC supplements, Aug. 2012, vol. 10, No. 3, pp. 4-6.
Extended Search Report for con-esponding European Patent Application No. 15740607.5.
Written Opinion for corresponding Singapore Application No. 11201605900V.
Dose modification of mFOLFOX6 regimen for colorectal cancer. European Journal of Hospital Pharmacy: Science and Practice, Mar. 12, 2012, vol. 19, pp. 258-259.
Jeon H.J. et al., Adjuvant Chemotherapy Using the FOLFOX Regimen in Colon Cancer. J Korean Soc Coloproctol., Jun. 30, 2011, vol. 27, No. 3, pp. 140-146.
Kato K. et al., A Multicenter Phase-II Study of 5-FU, Leucovorin and Oxaliplatin (FOLFOX6) in Patients with Pretreated Metastatic Colorectal Cancer. Jpn J Clin Oncol., Sep. 6, 2010, vol. 41, No. 1, pp. 63-68.
Office Action dated Dec. 3, 2019 in corresponding Singapore Application No. 11201605900V.

* cited by examiner

TREATMENT OF NEOPLASIA

CROSS REFERENCE TO RELATED APPLICATIONS

This application is a § 371 National State Application of PCT/AU2015/000037 filed Jan. 23, 2015 which claims priority to AU 2014900232 filed Jan. 24, 2014.

FIELD OF THE INVENTION

The present invention provides a method for treating colorectal cancer developed from the identification of an unexpected improved combination of known cancer therapies. It also relates to a therapeutic combination, which produces a greater treatment efficacy than previously known cancer therapies.

BACKGROUND ART

Cancer is one of the leading causes of death in the United States and many other countries. The disease is characterized by an abnormal proliferation of cell growth known as a neoplasm. Malignant cancers, in particular, can result in a serious disease state, which may threaten life. Significant research efforts and resources have been directed toward the elucidation of anticancer measures, including chemotherapeutic and radiotherapeutic agents, which are effective in treating patients suffering from cancer. Effective anticancer agents include those that inhibit or control the rapid proliferation of cells associated with neoplasms, those that effect regression or remission of neoplasms, and those that generally prolong the survival of patients suffering from neoplasia. The terms neoplasia, malignant neoplasia, neoplastic growth and cancer are used interchangeably throughout this document.

Of the vast array of malignant neoplasms, colorectal cancer is one of the most common. The liver is a dominant site of metastatic spread of colorectal cancer as a result of the portal venous drainage of the gut and is the main cause of death in these patients.

In colorectal cancer, liver metastases are linked to poor prognosis—death and recurrence are frequently attributable to liver metastases. Surgical resection of colorectal cancer liver metastases can result in cure, and produces 5-year survival of 27-39% and 10-year survival of 12-36%, as opposed to median survival of approximately 9 months if untreated. However, only 10-20% of patients with liver metastases from colorectal cancer are candidates for such surgery, and intra-hepatic and extra-hepatic relapse after liver resection is common.

Systemic chemotherapy is, therefore, used as first-line treatment in patients with non-resectable liver metastases, and in some cases can sufficiently down-size the tumour burden in patients with previously inoperable liver metastases so that they may be converted to candidates for potentially curative resection. Internationally accepted first-line chemotherapy regimens for patients with metastatic colorectal cancer include FOLFOX (combination of bolus and infusional 5-fluorouracil [5-FU], leucovorin [LV] and oxaliplatin (OXA)) and FOLFIRI (combination of bolus and infusional 5-FU, LV and irinotecan). These regimens provide median survival times of 16-20 months.

Selective Internal Radiation Therapy (SIRT) is an innovative radiation therapy for metastatic colorectal cancer, which involves the delivery of SIR-Spheres® (Sirtex Medical Limited, North Sydney, Australia) or Theraspheres that contain a β-emitter, yttrium-90, into the arterial supply of the liver. These microspheres are delivered via a trans-femoral hepatic artery catheter. In a randomised controlled trial, treatment of metastatic colorectal cancer with SIRT plus first-line 5-FU/LV chemotherapy resulted in a longer time-to-progression (18.6 months) compared with 5-FU/LV chemotherapy alone (3.6 months).

A therapeutic combination that extends the time to progression of colorectal cancer will have a significant benefit to patients. The present invention seeks to provide an improved method that delivers such a therapeutic combination.

SUMMARY OF THE INVENTION

The present invention provides an improved combination of known anticancer therapies which have utility, particularly in the treatment of primary and secondary liver cancer and, more specifically, secondary liver cancer deriving from the gastrointestinal tract such as secondary liver cancer deriving from colorectal cancer. In any chemotherapeutic treatment, delivery of the chemotherapeutic agent to a patient at a dose that minimises hepatotoxicity to noncancerous liver tissue while maximizing the chemotherapeutic benefit of the treatment is critical to a treatment regime.

According to the present invention there is provided a method for treatment of a cancer patient in need of treatment, which comprises the steps of:

(i) delivering to said patient on day one of a treatment regime:
   (a) a 2-hour infusion of oxaliplatin (OXA) at a dose of about 60 to 80 mg/m$^2$;
   (b) a 2-hour infusion of leucovorin (LV) at a dose of about 100 to 400 mg/m$^2$;
   (c) followed by a bolus of 5-fluorouracil (5-FU) at a dose of about 300 to 500 mg/m$^2$ and then an infusion of 5-FU for about 40 to 50 hours at a dose of about 2.0 to 2.6 g/m$^2$; and repeating step (i), if required, then
(ii) delivering selective internal radiation therapy (SIRT) to said patient between days 3 to 14 following either the commencement of step (i) or following the repeat of step (i);
(iii) repeating step (i) for three cycles at an interval of one to three weeks between treatment cycles; then
(iv) two weeks after the final treatment delivered in step (iii) delivering to said patient the following treatment:
   (a) a 2-hour infusion of OXA at a dose of about 80 to 100 mg/m$^2$;
   (b) a 2-hour infusion of LV at a dose of about 100 and 400 mg/m$^2$;
   (c) followed by a bolus of 5-FU at a dose of about 300 to 500 mg/m$^2$ and then an infusion of 5-FU for about 40 to 50 hours at a dose of about 2.0 to 2.6 g/m$^2$.

Desirably the above method is repeated until either liver hepatotoxicity becomes a problem or peripheral neuropathy becomes an issue for the patient.

According to an embodiment of the present invention there is provided a method for treatment of a cancer patient in need of treatment, which comprises the steps of:

(i) delivering to said patient on day one of a treatment regime:
   (d) a 2-hour infusion of OXA at a dose of about 60 to 80 mg/m$^2$;
   (e) a 2-hour infusion of LV at a dose of about 100 to 400 mg/m$^2$;

(f) followed by a bolus of 5-FU at a dose of about 300 to 500 mg/m² and then an infusion of 5-FU for about 40 to 50 hours at a dose of about 2.0 to 2.6 g/m²; and repeating step (i), if required, then (ii) delivering SIRT to said patient between days 3 to 14 following either the commencement of step (i) or following the repeat of step (i);

(iii) repeating step (i) for three cycles at an interval of one to three weeks between treatment cycles; then (iv) two weeks after the final treatment delivered in step (iii) delivering to said patient the following treatment:
  (d) a 2-hour infusion of OXA at a dose of about 80 to 100 mg/m²;
  (e) a 2-hour infusion of LV at a dose of about 100 and 400 mg/m²;
  (f) followed by a bolus of 5-FU at a dose of about 300 to 500 mg/m² and then an infusion of 5-FU for about 40 to 50 hours at a dose of about 2.0 to 2.6 g/m²; and (v) repeating step (iv) every 2 to 3 weeks, until the cancer is treated.

The dosing regimen used in the method should be selected to maximize safety and efficacy for the patient. Preferably the dosages selected will prolong the exposure duration to OXA, LV abd 5FU while maintaining efficacy outcomes.

It is to be understood that the SIRT described herein should not be limited to radioactive microparticles, but may be extended to any radioactive particles or materials of any sort, of which targeted antibodies labelled with a therapeutic radioactive material is one example, that are suitable for use in the treatment methods described herein.

Further, in an embodiment the method includes a step of treating the patient with one or more biological anticancer agents. Desirably that step is included at either cycle 1 or cycle 4 of the treatment regime. Preferably, the biological anticancer agent is an antibody or antibody fragment or antibody like molecule that is targeted against cells or the blood vessels supplying the cancer cells. For example, the agent may be an antibody or fragment thereof that targets EGF and VEGF, may also be used. Preferably, the anticancer agent is bevacizumab.

According to another embodiment of the present invention there is provided a method for treatment of a cancer patient in need of treatment, which comprises the steps of:

(i) delivering to said patient on day one of a treatment regime:
  (a) a 2-hour infusion of OXA at a dose of about 60 to 80 mg/m²;
  (b) a 2-hour infusion of LV at a dose of about 100 to 400 mg/m²;
  (c) followed by a bolus of 5-FU at a dose of about 300 to 500 mg/m² and then an infusion of 5-FU for about 40 to 50 hours at a dose of about 2.0 to 2.6 g/m²; and repeating step (i), if required, then (ii) delivering SIRT to said patient between days 3 to 14 following either the commencement of step (i) or following the repeat of step (i);

(iii) repeating step (i) for three cycles at an interval of one to three weeks between treatment cycles; then (iv) two weeks after the final treatment delivered in step (iii), delivering to said patient the following treatment:
  (a) a 2-hour infusion of OXA at a dose of about 80 to 100 mg/m²;
  (b) a 2-hour infusion of LV at a dose of about 100 and 400 mg/m²;
  (c) followed by a bolus of 5-FU at a dose of about 300 to 500 mg/m² and a 15 to 90 minute infusion of bevacizumab at about 5 to 10 mg/kg, followed by an infusion of 5-FU at a dose of about 2.0 to 2.6 g/m² for about 40 to 50 hours; and (v) repeating step (iv) every 2 to 3 weeks, until the cancer is treated.

Other chemotherapeutic agents that may be employed in the method include in addition to the stipulated chemotherapy regime include systemic chemotherapy drugs such as irinotecan or capecitabine.

The method may also include a step of treating the patient with anti-angiogenesis factors, i.e. drugs that inhibit blood supply of cancers.

Other aspects and advantages of the invention will become apparent to those skilled in the art from a review of the ensuing description.

DETAILED DISCLOSURE OF THE INVENTION

General

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively, and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

All references cited, including patents or patent applications are hereby incorporated by reference. No admission is made that any of the references constitute prior art.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout.

DESCRIPTION OF PREFERRED EMBODIMENTS

The Applicant has revealed that the co-administration to a patient of SIRT and systemic chemotherapy at doses and in a delivery regime that minimize hepatotoxicity from the chemotherapy, potentiates the radiation effect from the SIRT on liver cancer, while delivering a beneficial effect on extra-hepatic disease.

The present invention provides a method that has utility in the treatment of various forms of cancer and tumours, but particularly in the treatment of primary liver cancer and secondary liver cancer and, more specifically, secondary liver cancer deriving from the gastrointestinal tract, and most specifically secondary liver cancer deriving from colorectal cancer.

Preferably, the method is used for treating a patient with colorectal liver metastases.

As used herein "treatment" and "treated" includes:
(i) preventing a disease, disorder or condition from occurring in a patient who may be predisposed to the disease, disorder and/or condition but has not yet been diagnosed as having it;

(ii) inhibiting the disease, disorder or condition, i.e., arresting its development; or (iii) relieving or ameliorating the disease, disorder or condition, i.e., causing regression of the disease, disorder and/or condition.

According to the method the patient to be treated is preferably a mammal and is most preferably a human.

5-FU, LV and OXA Chemotherapy

In the method of the present invention, the amount of 5-FU, LV and OXA that is effective to treat the cancer is an amount that at least ameliorates cancer.

According to the present invention there is provided a method for treatment of a cancer patient in need of treatment, which comprises the steps of:

(i) delivering to said patient on day one of a treatment regime:
  (g) a 2-hour infusion of OXA at a dose of about 60 to 80 mg/m$^2$;
  (h) a 2-hour infusion of LV at a dose of about 100 to 400 mg/m$^2$;
  (i) followed by a bolus of 5-FU at a dose of about 300 to 500 mg/m$^2$ and then an infusion of 5-FU for about 40 to 50 hours at a dose of about 2.0 to 2.6 g/m$^2$; and repeating step (i), if required, then
(ii) delivering SIRT to said patient between days 3 to 14 following either the commencement of step (i) or following the repeat of step (i);
(iii) repeating step (i) for three cycles at an interval of one to three weeks between treatment cycles; then
(iv) two weeks after the final treatment delivered in step (iii) delivering to said patient the following treatment:
  (g) a 2-hour infusion of OXA at a dose of about 80 to 100 mg/m$^2$;
  (h) a 2-hour infusion of LV at a dose of about 100 and 400 mg/m$^2$;
  (i) followed by a bolus of 5-FU at a dose of about 300 to 500 mg/m$^2$ and then an infusion of 5-FU for about 40 to 50 hours at a dose of about 2.0 to 2.6 g/m$^2$.

Desirably the above method is repeated until either liver hepatotoxicity becomes a problem or peripheral neuropathy becomes an issue for the patient.

Accordingly to the present invention there is provided a method for treatment of a cancer patient in need of such treatment, which comprises the steps of:

(i) delivering to said patient on day one of a treatment regime:
  (a) a 2-hour infusion of OXA at a dose of about 60 to 80 mg/m$^2$;
  (b) a 2-hour infusion of LV at a dose of about 100 to 400 mg/m$^2$;
  (c) followed by a bolus of 5-FU at a dose of about 300 to 500 mg/m$^2$ and then an infusion of 5-FU for about 40 to 50 hours at a dose of about 2.0 to 2.6 g/m$^2$; and repeating step (i), if required, then
(ii) delivering SIRT to said patient between days 3 to 14 following either the commencement of step (i) or following the repeat of step (i);
(iii) repeating step (i) for three cycles at an interval of one to three weeks between treatment cycles; then
(iv) following about two weeks from the final treatment delivered in step (iii) delivering to said patient the following treatment:
  (a) a 2-hour infusion of OXA at a dose of about 80 to 100 mg/m$^2$;
  (b) a 2-hour infusion of LV at a dose of about 100 and 400 mg/m$^2$;
  (c) followed by a bolus of 5-FU at a dose of about 300 to 500 mg/m$^2$ and then an infusion of 5-FU for about 40 to 50 hours at a dose of about 2.0 to 2.6 g/m$^2$; and
(v) repeating step (iv) every 2 to 3 weeks, until the cancer is treated.

Desirably step (v) in the method of the invention is repeated until either liver hepatotoxicity becomes a problem or peripheral neuropathy becomes an issue for the patient. Hepatotoxicity of tissues peripheral to cancerous tissue may become apparent as a result of excessive chemotherapy in a subject.

The assessment of liver toxicity is a rather complex process particularly when using chemotherapeutic agents. The current methods usually comprise clinical investigations (e.g. ultrasonography), pathological and histo-pathological investigations as well as a biochemical analysis. A state-of the-art evaluation of the drug-induced liver toxicity is described in the CDER/CBER Guidance for Industry: Drug-Induced Liver Injury: Premarketing Clinical Evaluation, July 2009 as well as in the EMEA (CHMP) Reflection paper on non-clinical evaluation of drug-induced liver injury (DILI), 24 Jun. 2010 (Doc Ref EMEA/CHMP/SWP/150115/2006).

According to this method the doses of OXA administered to a patient in the initial three cycles of the invention will be less than the dose of OXA administered in the fourth and subsequent cycles of drug administration. The primary safety concern is that the OXA in the chemotherapy regimen is a radio-sensitising agent, which when used in combination with SIRT results in toxicity at doses greater than initially delivered.

Further according to the invention OXA doses in the fourth and subsequent cycles should be more than the first three cycles but minimized as much as possible to maximise the time that patients can receive protocol chemotherapy before peripheral neuropathy becomes an issue (which necessitates the removal of OXA).

The method contemplates either a single or multiple doses of 5-FU, LV and OXA delivered according to the treatment regime to impair the symptoms of the cancer being treated. For example, impairment of symptoms of the cancer may be ameliorated by diminishing pain or discomfort suffered by the patient; by extending the survival of the patient beyond that which would otherwise be expected in the absence of such treatment; by inhibiting or preventing the development or spread of the cancer; or by limiting, suspending, terminating, or otherwise controlling the maturation and proliferation of cells in the cancer.

Notably, the amounts of 5-FU, LV and OXA effective to treat cancer in a patient in need of treatment will vary depending on the type of SIRT used, as well as the particular factors of each case, including the type of cancer, the stage of the cancer, the patient's weight, the severity of the patient's condition, and the method of administration. These amounts can be readily determined by the skilled artisan.

Desirably, OXA is delivered to the patient in the initial three treatment cycles at a dose of about 60 to 80 mg/m$^2$. Reference to the use of the term "about" in this statement seeks to import a level of variability into the treatment regime that is consistent with the manner in which a doctor might vary the OXA regime depending on the needs of a patient. For example a dose of OXA at 54, 55, 56, 57, 58 or 59 mg/m$^2$ can appropriately be used in the treatment regime and such doses should be considered within the scope of the present invention. Similarly, doses of OXA at 81, 82, 83, 84, 85, 86, 87, or 88 mg/m$^2$ can also appropriately be used in the first treatment cycle. Preferably, the dose will reside within the range of 60 to 80 mg/m$^2$. In a preferred form of the invention the dose of OXA will be closer towards the lower end of the stipulated range. Such doses of OXA include doses selected from 60, 61, 62, 63, 64, 65, 66, 67, 68, 69, 70, 71, 72, 73, 74, 75, 76, 77, 78, 79, 80 mg/m$^2$.

According to the method of the invention, in the fourth cycle of treatment, the dose of OXA is increased to at least about 80 to 100 mg/m$^2$. Reference to the use of the term "about" in this statement seeks to import a level of variability into the treatment regime that is consistent with the manner in which a doctor might vary the OXA regime depending on the needs of a patient. For example a dose of OXA at 77, 78 or 79, 80, 81, 82, 83 or 84 mg/m$^2$ can appropriately be used in the treatment regime and such doses should be considered within the scope of the present invention. Similarly, doses of OXA at 101, 102, 103, 104, 105, 106, 107, or 108, 109 or 110 mg/m$^2$ can also appropriately be used in the first treatment cycle. Preferably, the dose will reside within the range of 80 to 100 mg/m$^2$. In a preferred form of the invention the dose of OXA will be closer towards the lower end of the stipulated range. Such doses of OXA include 80, 81, 82, 83, 84, 85, 86, 87, 88, 89, 90, 91, 92, 93, 94, 95, 96, 97, 98, 99, 100 mg/m$^2$.

In an embodiment of the invention, the dose of OXA administered in the initial three cycles of the invention is about 60 mg/m$^2$ while the dose administered in the fourth cycle is 85 mg/m$^2$. According to this embodiment of the invention OXA is delivered at a dose of 60 mg/m$^2$ for the first three cycles of chemotherapy, and in subsequent cycles is increased to a dose of 85 mg/m$^2$. The primary safety concern is that the OXA in the chemotherapy regimen is a radio-sensitising agent, which when used in combination with SIR-Spheres® or Theraspheres treatment or locally delivered Y90 treatment results in toxicity at doses >60 mg/m$^2$.

Further according to this embodiment of the invention OXA doses in the fourth and subsequent cycles should be 85 mg/m$^2$ rather than the dose of 100 mg/m$^2$, this will maximise the time that patients can receive protocol chemotherapy before peripheral neuropathy becomes an issue (which necessitates the removal of OXA).

Desirably, the dose of LV delivered to the patient in the initial three treatment cycles and in the fourth cycle is at a dose of about 100 to 400 mg/m$^2$. Reference to the use of the term "about" in this statement seeks to import a level of variability into the treatment regime that is consistent with the manner in which a doctor might vary the LV regime depending on the needs of a patient. For example a dose of LV at 90, 91, 92, 93, 94, 95, 96, 97, 98 or 99 mg/m$^2$ can appropriately be used in the treatment regime and such doses should be considered within the scope of the present invention. Similarly, doses of LV at 401, 402, 403, 404, 405, 406, 407, up to 428 mg/m$^2$ inclusive, can also appropriately be used in the first treatment cycle. Preferably, the dose will reside within the range of 100 and 400 mg/m$^2$. In a preferred form of the invention the dose of LV will be closer towards the lower end of the stipulated range, eg 100 to 200 mg/m$^2$. By way of illustration doses of LV include 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400 mg/m$^2$ as well as every dose in between these specified doses.

Desirably, the bolus of 5-FU delivered to the patient in the initial three treatment cycles and in the fourth cycle is at a dose of about 300 to 500 mg/m$^2$. Reference to the use of the term "about" in this statement seeks to import a level of variability into the treatment regime that is consistent with the manner in which a doctor might vary the LV regime depending on the needs of a patient. For example a dose of 5-FU in the bolus can be at 250, 260, 270, 280, 290 mg/m$^2$ can appropriately be used in the treatment regime and such doses should be considered within the scope of the present invention. Similarly, doses of 5-FU in the order of 510, 520, 530, 540 and 550 mg/m$^2$ inclusive, can also appropriately be used in the first treatment cycle. Preferably, the dose will reside within the range of 300 and 500 mg/m$^2$. By way of illustration doses of 5-FU include 300, 310, 320, 330, 340, 350, 360, 370, 380, 390, 400, 410, 420, 430, 440, 450, 460, 470, 480, 490, 500 mg/m$^2$ as well as every dose in between these specified doses. In a preferred form of the invention the dose of 5-FU in the bolus will be about 400 mg/m$^2$.

Desirably, the continuous infusion of 5-FU that is delivered to the patient in the initial three treatment cycles and in the fourth cycle is at a dose of about 2.0 to 2.6 g/m$^2$. Reference to the use of the term "about" in this statement seeks to import a level of variability into the treatment regime that is consistent with the manner in which a doctor might vary the LV regime depending on the needs of a patient. For example a dose of 5-FU in the continuous infusion can be at 1.5, 1.6, 1.7, 1.8, 1.9 or 2.0 g/m$^2$ can appropriately be used in the treatment regime and such doses should be considered within the scope of the present invention. Similarly, doses of 5-FU in the continuous infusion in the order of 2.6, 2.7, 2.8 or 2.9 g/m$^2$ inclusive, can also appropriately be used in the first treatment cycle. Preferably, the dose will reside within the range of 2.0 to 2.6 g/m$^2$. By way of illustration doses of 5-FU include 2.1, 2.2, 2.3, 2.4 and 2.5 g/m$^2$. In a preferred form of the invention the dose of 5-FU in the bolus will be about 2.4 g/m$^2$.

The time period over which the continuous infusion of 5-FU is delivered to the patient may vary from about 40 to 50 hours. A physician period will preferably determine the delivery time. In a desirable form of the invention the delivery time is selected from the group consisting of 40, 41, 42, 43, 44, 45, 46, 47, 48, 49 or 50 hours. Most preferably the infusion is for 46 hours.

It will be appreciated that the dose of chemotherapeutic agent delivered to the patient according to the above treatment regime may vary within the various dose ranges specified. Moreover, the dose of chemotherapeutic agent delivered to a patient may vary between treatment cycles. Ideally, variation of the dose of drug delivered accommodates for hepatotoxicity. In this respect the dose of drug delivered in a treatment cycle should seek to keep to a minimum the hepatotoxicity in that treatment cycle.

In a preferred form of the invention there is provided a method of treatment of a cancer patient in need of such treatment, which comprises the steps of:
  (i) delivering to said patient on day one of a treatment regime:
    (a) a 2-hour infusion of OXA at a dose of about 60 mg/m$^2$;
    (b) a 2-hour infusion of LV at a dose of about 200 mg/m$^2$;
    (c) followed by a bolus of 5-FU at a dose of 400 mg/m$^2$ and then a 46-hour infusion of 5-fluorouracil at a dose of 2.4 g/m$^2$; and then
  (ii) delivering SIRT to said patient on day 3 or 4 following the commencement of step (i);
  (iii) repeating step (i) three times at an interval of one to three weeks between treatment cycles; then
  (iv) following about two weeks from the final treatment delivered in step (iii) delivering to said patient the following treatment:

(a) a 2-hour infusion of OXA at a dose of about 85 mg/m$^2$;

(b) a 2-hour infusion of LV at a dose of between 200 mg/m$^2$;

(c) followed by a bolus of 5-FU at a dose of 400 mg/m$^2$ and then a 46-hour infusion of 5-FU at a dose of 2.4 g/m$^2$; and (v) repeating step (iv) every 2 to 3 weeks, until the cancer is treated.

Chemotherapeutic agents used in the treatment according to the present invention may be administered to a patient by known procedures, including, but not limited to, oral administration, parenteral administration (e.g., intramuscular, intraperitoneal, intravascular, intravenous, or subcutaneous administration), and transdermal administration. Preferably, the 5-FU, LV and OXA agents are administered parenterally.

Selective Internal Radiation Therapy (SIRT)

According to the invention the person skilled in the art will appreciate that SIRT may be applied by any of a range of different methods, some of which are described in U.S. Pat. Nos. 4,789,501, 5,011,677, 5,302,369, 6,296,831, 6,379,648, or WO applications 200045826, 200234298 or 200234300 (incorporated herein by reference). Accordingly, administration of radionuclide doped microparticles may be by any suitable means, but preferably by delivery via the relevant artery. For example, in treating liver cancer, administration is preferably by insertion of a catheter into the hepatic artery. Pre or co-administration of another agent may prepare the tumour for receipt of the particulate material, for example a vasoactive substance, such as angiotension-2 to redirect arterial blood flow into the tumour. Delivery of the particulate matter may be by single or multiple doses, until the desired level of radiation is reached.

Generally, SIRT is administered on only one or two occasions whereas treatment with 5FU, LV and OXA are administered at or about the time of SIRT and are continued as an ongoing treatment.

The radionuclide doped microparticles need not be limited to any particular form or type of microparticle. So, for example, the radionuclide doped microparticles suitable for use in the invention may comprise any material capable of receiving a radionuclide such as through impregnation, absorbing, coating or more generally bonding the radionuclide with the microparticle or material used to carry the radionuclide.

In one particular form of the invention the microparticles are prepared as polymeric particles. In another form of the invention the microparticles are prepared as ceramic particles (including glass (eg Theraspheres)). In another, they are prepared from chitosan. In another they are formed of yttria. In another they are formed substantially from silicon. In another they are formed from proteins. In another they are formed from antibodies.

Where the microparticles are prepared as a polymeric matrix they will preferably have a stably incorporated radionuclide. More preferably the radionuclide will be incorporated by precipitation of the radionuclide as a salt. A description of such particles including methods for their production and formulation as well as their use is provided in co-owned European application number 200234300, of which the teachings therein are expressly incorporated herein by reference.

Where the particles are based on silicon the radionuclide will preferably be stably incorporated into the silicon matrix or within the pores or micropores of the matrix or coated onto the matrix.

Where the particles are based on yttria, the radionuclide will preferably be stably incorporated into the yttria matrix or coated onto the surface.

Where the microparticles are ceramic particles (including glass) the selected particles will usually possess the following properties:

(1) the particles will generally be biocompatible, such as calcium phosphate-based biomedical ceramics or glass, or aluminium-boro silicate glass, or silicate based glass.

(2) the particles will generally comprise a radionuclide that preferably emits radiation of sufficiently high energy and with an appropriate penetration distance in tissue, which are capable of releasing their energy complement within the tumour tissue to effectively kill the cancer cells and to minimize damage to adjacent normal cells or to attending medical personnel. The level of radiation activity of the ceramic or glass will be selected and fixed based upon the need for therapy given the particular cancer involved and its level of advancement. The ideal half-life of the radionuclides is somewhere between hours (e.g. Holmium 166) and months. On the one hand, it is impractical to treat tumours with radionuclides having too short a half-life, this characteristic limiting therapy efficiency. On the other hand, in radiotherapy it is generally difficult to trace and control radionuclides having a long half-life.

(3) Third, the particles must be of a suitable size. The size of the particles for treatment depends upon such variables as the selected method of introduction into the tumour.

There are many processes for producing small granular ceramic or glass particles. One of these involves the introduction of small amounts of the ceramic particles passing through a high-temperature melting region. Ceramic spherules are yielded by surface tension during melting. After the solidification, condensation, collection and sorting processes, ceramic spherules of various sizes can be obtained. The particle size of ceramic spheroids can be controlled by the mass of granules introduced into the high-temperature melting region or can be controlled by collecting spheroids of various sizes through the selection of sedimentation time during liquid-sedimentation.

The ceramic or glass materials for preparing those particles can be obtained commercially or from ultra-pure ceramic raw materials if the commercial products do not meet specifications for one reason or another. The ceramic or glass particles for radiation exposure in this invention can be yielded by traditional ceramic processes, which are well known by those skilled in this art. The ceramic processes such as solid-state reaction, chemical co-precipitation, sol-gel, hydrothermal synthesis, glass melting, granulation, and spray pyrolysis can be applied in this invention for the production of specific particles.

The microparticles of the invention be they polymer, ceramic, glass or silicon based or other can be separated by filtration or other means known in the art to obtain a population of microparticles of a particular size range that is preferred for a particular use.

The radionuclide which is incorporated into the microparticles in accordance with the present invention is preferably yttrium-90, but may also be any other suitable radionuclide of which holmium, samarium, iodine, phosphorous, iridium, lutetium and rhenium are some examples.

The amount of microparticles used in the method and which will be required to provide effective treatment of a neoplastic growth will depend on the radionuclide used in the preparation of the microparticles. By way of example, an amount of yttrium-90 activity that will result in an inferred radiation dose to the normal liver of approximately 80 Gy may be delivered per lobe. This equates to an activity of microparticles used to treat metastases in both lobes of the liver of typically between 1.2 and 2.4 GBq.

Because the radiation from SIRT is delivered as a series of discrete point sources, the dose of 80 Gy is an average dose with many normal liver parenchymal cells receiving much less than this dose. Alternate doses of radiation may be delivered depending on the disease state and the physician's treatment needs. Such variation of radiation doses obtained by altering the amount of microparticles used will be something that a skilled artisan will know how to determine.

The term microparticle is used in this specification as an example of a particulate material, it is not intended to limit the invention to microparticles of any particular shape or configuration. A person skilled in the art will, however, appreciate that the shape of the particulate material will preferably be substantially spherical, but need not be regular or symmetrical in shape and could be of any shape or size.

In addition to the identified chemotherapeutic agents and radionuclide doped microparticles the invention may also include an effective treatment of immunomodulators and other agents as part of the therapy. Illustrative immunomodulators suitable for use in the invention are alpha interferon, beta interferon, gamma interferon, interleukin-2, interleukin-3, tumour necrosis factor, and the like.

In a highly preferred form of the invention the SIRT microparticles are SIR-Spheres™ microspheres (obtained from Sirtex Medical Pty Ltd) These microparticles consist of biocompatible resin microspheres containing yttrium-90 with a size between 20 and 60 microns in diameter. Yttrium-90 (90Y) is a high-energy pure beta-emitting isotope with no primary gamma emission. The maximum energy of the beta particles is 2.27 MeV with a mean of 0.93 MeV. The maximum range of emissions in tissue is 11 mm with a mean of 2.5 mm. The half-life is 64.1 hours. In use requiring the isotope to decay to infinity, 94% of the radiation is delivered in 11 days leaving only background radiation with no therapeutic value. SIR-Spheres™ microspheres themselves are a permanent implant. Each device is for single patient use. The prescribed activity of SIR-Spheres™ microspheres used to treat metastases in both lobes of the liver was typically between 1.2 and 2.4 GBq.

These microparticles do not exhibit pharmacodynamics in the classic sense, but induce cell damage by emitting beta radiation (mean penetration in tissue 2.5 mm). Once implanted, this microparticles remain within the vasculature of tumours, with small amounts within the vasculature of normal tissue. The microparticles are not phagocytised nor do they dissolve or degrade after implantation. High dose radiation emitted from the device is cytocidal to cells within the range of the radiation. After the yttrium-90 has decayed, the non-radioactive microparticles remain intact and are not removed from the body.

Microparticles may interact with other cytotoxic agents. In such a situation the microparticles may be co-administered concomitantly with chemotherapeutic regimens. This applies to chemotherapeutic agents applied for the purpose of managing either the same tumours targeted by the microparticles, or distant metastases. This interaction may be exploited to the benefit of the patient, in that there can be an additive toxicity on tumour cells, which can enhance the tumour cell kill rate. This interaction can also lead to additive toxicity on non-tumourous cells.

Biological Anticancer Agents

Further, the method may also include a step of treating the patient with one or more biological anticancer agents such as antibodies, fragments thereof or antibody like molecules targeted against a variety of cancer cells or the blood vessels supplying the cancer cells. For example antibodies, fragments thereof or antibody like molecules target EGF or VEGF. Preferably, the anticancer agent is bevacizumab.

Accordingly in an embodiment of the present invention there is provided a method for treatment of a cancer patient in need of treatment, which comprises the steps of:
(i) delivering to said patient on day one of a treatment regime:
  (a) a 2-hour infusion of OXA at a dose of about 60 to 80 mg/m$^2$;
  (b) a 2-hour infusion of LV at a dose of about 100 to 400 mg/m$^2$;
  (c) followed by a bolus of 5-FU at a dose of about 300 to 500 mg/m$^2$ and then an infusion of 5-FU for about 40 to 50 hours at a dose of about 2.0 to 2.6 g/m$^2$; and repeating step (i), if required, then
(ii) delivering SIRT to said patient between days 3 to 14 following either the commencement of step (i) or following the repeat of step (i);
(iii) repeating step (i) for three cycles at an interval of one to three weeks between treatment cycles; then
(iv) two weeks after the final treatment delivered in step (iii) delivering to said patient the following treatment:
  (a) a 2-hour infusion of OXA at a dose of about 85 to 100 mg/m$^2$;
  (b) a 2-hour infusion of LV at a dose of about 100 and 400 mg/m$^2$;
  (c) followed by a bolus of 5-FU at a dose of about 300 to 500 mg/m$^2$ and a 15 to 90 minute infusion of bevacizumab at about 5 to 15 mg/kg, followed by an infusion of 5-FU at a dose of about 2.0 to 2.6 g/m$^2$ for about 40 to 50 hours; and
(v) repeating step (iv) every 2 to 3 weeks, until the cancer is treated.

The biological anticancer agent(s) may be administered at any dose that is recommended for treating patients with cancer. Where the biological anticancer agent is bevacizumab preferably a dose of about 5 to 10 mg/kg is delivered to said patient.

The time over which the agent is delivered to a patient will be varied depending on the patient and severity of treatment required. In a preferred form of the invention where bevacizumab is administered per the above dose regime the agent treatment time is 30 to 60 minutes.

Bevacizumab therapy may be delivered at any one or more of the various cycles of treatment. Desirably, bevacizumab therapy is delivered with the first cycle of therapy or in the last cycle. In a highly preferred form of the invention bevacizumab therapy is delivered in the last cycle of therapy immediately after OXA therapy. In an alternate form of the invention bevacizumab is administered 6 weeks after SIRT treatment.

In a highly preferred form, the invention resides in a method for treatment of a cancer patient in need of treatment, which comprises the steps of:
(i) delivering to said patient on day one of a treatment regime:
  (a) a 2-hour infusion of OXA at a dose of about 60 mg/m$^2$;
  (b) a 2-hour infusion of LV at a dose of about 200 mg/m$^2$;

(c) followed by a bolus of 5-FU at a dose of about 400 mg/m² and then an infusion of 5-FU for about 46 hours at a dose of about 2.4 g/m²; and then (ii) delivering SIRT to said patient on day 3 or 4 following the commencement of step (i);

(iii) repeating step (i) for three cycles at an interval of one to three weeks between treatment cycles; then (iv) two weeks after the final treatment delivered in step (iii) delivering to said patient the following treatment:
(a) a 2-hour infusion of OXA at a dose of about 85 mg/m²;
(b) a 2-hour infusion of LV at a dose of about 200 mg/m²;
(c) followed by a bolus of 5-FU at a dose of about 400 mg/m² and a 30 to 60 minute infusion of bevacizumab at about 5 to 10 mg/kg, followed by an infusion of 5-FU at a dose of about 2.4 g/m² for about 46 hours; and (v) repeating step (iv) every 2 to 3 weeks, until the cancer is treated.

EXAMPLES

Further features of the present invention are more fully described in the following non-limiting example. It is to be understood that this description is included solely for the purposes of exemplifying the present invention. It should not be understood in any way as a restriction on the broad description of the invention as set out above.

Patients:

Patients with colorectal liver metastases either with or without extra-hepatic metastases were enrolled in this study. Patients were between 45 and 70 years of age, had histologically proven colorectal adenocarcinoma, and unequivocal CT scan evidence of liver metastases that could not be treated by resection or any locally ablative technique.

Investigations:

All patients underwent a pre-treatment spiral CT scan of the whole abdomen and either a CT scan of the chest or chest X-ray and blood tests to assess haematologic, renal and liver function and serum CEA.

Treatment Regime

Systemic Chemotherapy Experimental Arm:

Where SIRT implantation was performed in cycle 1, systemic chemotherapy was given as detailed below:

Cycles 1-3:
  Day 1
    Hour 0: Oxaliplatin 60 mg/m² in 250 ml glucose 5%, 2-hour IV infusion
    Hour 0: Leucovorin 200 mg/m² in 250 ml glucose 5%, 2-hour IV infusion
    Hour +2: 5-FU bolus 400 mg/m², IV bolus
    Hour +2: 5-FU continuous infusion 2400 mg/m², 46-hour cont. IV infusion
  Was repeated every 14 days for first 3 cycles.

Cycles 4 onward:
  Day 1
    Hour 0: Oxaliplatin 85 mg/m² in 250 ml glucose 5%, 2-hour IV infusion
    Hour 0: Leucovorin 200 mg/m² in 250 ml glucose 5%, 2-hour IV infusion
    Hour +2: 5-FU bolus 400 mg/m², IV bolus
    Hour +2: 5-FU continuous infusion 2400 mg/m², 46-hour cont. IV infusion If SIRT implantation was performed in cycle 2, systemic chemotherapy was given as detailed below:

Cycle 1:
  Day 1
    Hour 0: Oxaliplatin 85 mg/m² in 250 ml glucose 5%, 2-hour IV infusion
    Hour 0: Leucovorin 200 mg/m² in 250 ml glucose 5%, 2-hour IV infusion
    Hour +2: 5-FU bolus 400 mg/m², IV bolus
    Hour +2: 5-FU continuous infusion 2400 mg/m², 46-hour cont. IV infusion Cycles 2-4:
  Day 1
    Hour 0: Oxaliplatin 60 mg/m² in 250 ml glucose 5%, 2-hour IV infusion
    Hour 0: Leucovorin 200 mg/m² in 250 ml glucose 5%, 2-hour IV infusion
    Hour +2: 5-FU bolus 400 mg/m², IV bolus
    Hour +2: 5-FU continuous infusion 2400 mg/m², 46-hour cont. IV infusion Cycles 5 onward:
  Day 1
    Hour 0: Oxaliplatin 85 mg/m² in 250 ml glucose 5%, 2-hour IV infusion
    Hour 0: Leucovorin 200 mg/m² in 250 ml glucose 5%, 2-hour IV infusion
    Hour +2: 5-FU bolus 400 mg/m², IV bolus
    Hour +2: 5-FU continuous infusion 2400 mg/m², 46-hour cont. IV infusion Chemotherapy dose and schedule modifications: Chemotherapy doses were modified and/or delayed according to Tables 1 and 2 and the guidelines below.

TABLE 1

Dose Modification Due to Toxicity (excludes neurosensory toxicity)

| | Initial Doses (mg/m²/cycle) | | |
|---|---|---|---|
| | 5-FU IV bolus 400 | 5-FU IV continuous infusion 2400 | Oxaliplatin 85 |
| Type of Toxicity (NCI-CTC Grade) | Dose modifications of study drugs (mg/m²/cycle) (LV dose should not be modified) | | |
| Haemoglobin (any grade) | none | none | None |
| White blood cells (any grade) | none | none | None |
| Neutrophils grade 3 or 4 | 300 | 1800 | 65 |
| Platelets grade 3 or 4 | 300 | 1800 | 65 |
| Nausea and/or vomiting grade 4 despite adequate anti-emetic treatment | Stop treatment. | | |
| Diarrhoea grade 3 | 300 | 1800 | None |
| Diarrhoea grade 4* | 300 | 1800 | 65 |
| Stomatitis grade 3 | 300 | 1800 | None |
| Stomatitis grade 4* | 300 | 1800 | 65 |
| Heart ≥ grade 2 | Stop treatment. | | |
| Skin grade 3 or 4 | 300 | 1800 | None |
| Allergy grade 3 or 4 | Stop treatment. | | |
| Neurocerebellar | Stop treatment. | | |
| Alopecia (any grade) | none | none | None |
| Local intolerance (any grade) | none | none | None |
| Other toxicity clearly drug related: | | | |
| grade 1 or 2 | none | none | none |
| grade 3 | 300 | 1800 | 65 |
| grade 4 | Stop treatment | Stop treatment | Stop treatment |

*or repeated grade 3 after 5-FU dose reduction

Once a dose was reduced due to toxicity according to the table above, re-escalation in subsequent cycles was not allowed. However, a temporary reductions in dose was permissible at investigator discretion for patients in the SIR-Spheres™ microspheres arm in the first cycles, when toxicities were clearly attributable to the implantation of SIR-Spheres microspheres (eg transient leucopaenia).

Oxaliplatin induced neurotoxicity: The oxaliplatin dose was reduced in the next cycle according to the specific grade of peripheral neuropathy observed after a given cycle of chemotherapy (Table 2).

TABLE 2

Dose Modification of Oxaliplatin Due to Peripheral Neuropathy

| | Dose modification of oxaliplatin (mg/m$^2$/cycle) Duration of Peripheral Neuropathy | | |
|---|---|---|---|
| Type of Toxicity | ≤7 days | Non persistent >7 and <14 days | Persistent between courses |
| Cold-related dysaesthesia | none | none | none |
| Paraesthesia | none | none | Stop until recovery, then restart at 75 |
| Paraesthesia associated with pain or functional impairment | none | 75 | Stop treatment |

Upon evidence of oxaliplatin induced dose limiting peripheral neuropathy, chemotherapy was continued with 5-FU/LV alone. If oxaliplatin treatment was interrupted due to cumulative neurotoxicity, it was reintroduced upon symptoms relief, at Investigator discretion at any time prior to objective evidence of disease progression Experimental Arm: SIRT Plus Systemic Chemotherapy Selective internal radiation therapy (SIRT): The SIRT procedure comprised of a baseline mapping angiogram to determine the vascular anatomy of the liver and potential coil embolisation of afferent vessels that may arise from the hepatic arteries and supply other organs, followed by the actual implantation of the SIR-Spheres™ microspheres which occurred 3-14 days after the baseline mapping angiogram.

Assessing patient suitability for SIRT: Patients randomised to receive the combination of SIR-Spheres™ microspheres plus systemic chemotherapy were assessed in order to determine their suitability for SIRT.

Patients unable to receive SIRT received treatment as in the control arm—and their safety and efficacy data recorded—and analysed as in the SIRT arm (intention to treat analysis). Note that these patients received the full dose of oxaliplatin (85 mg/m2) from cycle 1 and were not required to have the temporary dose reduction delivered for patients randomised to the SIRT arm. These patients also started with bevacizumab treatment immediately.

a. Hepatic Angiogram

Patients underwent a preliminary mapping angiogram of the liver, between 3 and 14 days prior to the implantation of SIR-Spheres™ microspheres to determine the vascular anatomy of the liver and to perform a nuclear medicine 'break-through' scan. The hepatic angiogram provides a road map of the arterial supply of the liver in order to plan delivery of the SIR-Spheres™ microspheres. The hepatic angiogram was performed together with the nuclear medicine 'break-through' scan and results were available prior to the implantation of SIR-Spheres™ microspheres.

b. Liver-To-Lung Nuclear Medicine Break-Through Scan

In about 3% of patients with liver metastases from colorectal cancer there was significant arterio-venous shunts in the liver which allowed more than 10% of the SIR-Spheres™ microspheres injected into the liver to pass through the liver and lodge in the lungs. As excessive liver-to-lung shunting may cause radiation damage to the lungs, a nuclear medicine 'break-through' scan was performed in all patients to exclude this level of arterio-venous flow.

The percentage of technetium-99m labelled macro-aggregated albumin (MAA) that has escaped through the liver and lodged in the lungs was then be expressed as a 'percent lung shunting'. Normally this is less than 10% in patients with liver metastases from colorectal cancer. The total lung radiation dose delivered by SIR-Spheres™ microspheres must be kept below 30 Gy in order to ensure that the patient does not develop radiation pneumonitis. Therefore, according to the prescribed activity tables provided below, a reduction in prescribed activity was applied if the liver-to-lung shunting is greater than 10%. SIRT treatment is contraindicated if a shunt >20% exists.

Calculation of SIR-Spheres™ microspheres activity: The percentage tumour involvement in the liver was estimated from the baseline CT scan of the liver.

The prescribed activity of SIR-Spheres™ microspheres was determined from Tables 3, 4 and 5 and was based on the patient's body surface area (BSA), the percentage tumour involvement in the liver, and the percentage liver-to-lung shunt. The prescribed activity of SIR-Spheres™ microspheres used to treat metastases in both lobes of the liver was typically between 1.2 and 2.4 GBq The following Tables 3, 4 and 5 determine the patient-specific prescribed activities of SIR-Spheres™ microspheres. Note that the prescribed activity determined from these tables was intended for treatment of the whole liver. If treatment was planned to be restricted to one lobe of the liver then the prescribed activity was decreased to account for the volume of the lobe as a fraction of the total liver volume.

To determine the prescribed activity of SIR-Spheres™ microspheres to be implanted the Investigator needed to know the following information about the patient to be treated:

1. Liver-to-lung break through (%)
2. Body surface area (BSA)
3. Tumour involvement (%)

The appropriate table, as determined by the liver-to-lung break through, can then be cross-indexed in order to calculate the prescribed activity of SIR-Spheres™ microspheres (GBq) to be implanted.

The three tables are each based on different liver-to-lung break through percentages. These are:

Table 3: 0-10% break through
Table 4: 11-15% break through
Table 5: 16-20% break through If the liver-to-lung break through is higher than 20% then the patient was ineligible for SIR-Spheres™ microspheres treatment.

TABLE 3

0-10% break through
Administered Dose Calculator (GBq)
0-10% Lung Break-Through

| | | Percentage Tumour Involvement | | | | | | | | | | | | | | | |
|---|---|---|---|---|---|---|---|---|---|---|---|---|---|---|---|---|---|
| | | 0-5 | 6-10 | 11-15 | 16-20 | 21-25 | 26-30 | 31-35 | 36-40 | 41-45 | 46-50 | 51-55 | 56-60 | 61-65 | 66-70 | 71-75 | 76-80 |
| BSA | 1.30-1.35 | 0.7 | 0.8 | 1.0 | 1.2 | 1.3 | 1.4 | 1.5 | 1.5 | 1.5 | 1.5 | 1.4 | 1.3 | 1.3 | 1.2 | 1.1 | 1.1 |
| | 1.36-1.40 | 0.7 | 0.9 | 1.0 | 1.2 | 1.3 | 1.4 | 1.5 | 1.5 | 1.5 | 1.5 | 1.5 | 1.4 | 1.3 | 1.2 | 1.2 | 1.1 |
| | 1.41-1.45 | 0.7 | 0.9 | 1.1 | 1.2 | 1.4 | 1.5 | 1.6 | 1.6 | 1.6 | 1.6 | 1.5 | 1.4 | 1.4 | 1.3 | 1.2 | 1.2 |
| | 1.46-1.50 | 0.8 | 0.9 | 1.1 | 1.3 | 1.4 | 1.5 | 1.6 | 1.7 | 1.7 | 1.6 | 1.6 | 1.5 | 1.4 | 1.3 | 1.3 | 1.2 |
| | 1.51-1.55 | 0.8 | 1.0 | 1.1 | 1.3 | 1.5 | 1.6 | 1.7 | 1.7 | 1.7 | 1.7 | 1.6 | 1.5 | 1.5 | 1.4 | 1.3 | 1.2 |
| | 1.56-1.60 | 0.8 | 1.0 | 1.2 | 1.4 | 1.5 | 1.6 | 1.7 | 1.8 | 1.8 | 1.7 | 1.7 | 1.6 | 1.5 | 1.4 | 1.3 | 1.3 |
| | 1.61-1.65 | 0.8 | 1.0 | 1.2 | 1.4 | 1.6 | 1.7 | 1.8 | 1.8 | 1.8 | 1.8 | 1.7 | 1.6 | 1.6 | 1.5 | 1.4 | 1.3 |
| | 1.66-1.70 | 0.9 | 1.1 | 1.3 | 1.4 | 1.6 | 1.7 | 1.8 | 1.9 | 1.9 | 1.8 | 1.8 | 1.7 | 1.6 | 1.5 | 1.4 | 1.4 |
| | 1.71-1.75 | 0.9 | 1.1 | 1.3 | 1.5 | 1.7 | 1.8 | 1.9 | 1.9 | 1.9 | 1.9 | 1.8 | 1.7 | 1.6 | 1.5 | 1.5 | 1.4 |
| | 1.76-1.80 | 0.9 | 1.1 | 1.3 | 1.5 | 1.7 | 1.8 | 1.9 | 2.0 | 2.0 | 1.9 | 1.9 | 1.8 | 1.7 | 1.6 | 1.5 | 1.4 |
| | 1.81-1.85 | 0.9 | 1.1 | 1.4 | 1.6 | 1.8 | 1.9 | 2.0 | 2.0 | 2.0 | 2.0 | 1.9 | 1.8 | 1.7 | 1.6 | 1.5 | 1.5 |
| | 1.86-1.90 | 1.0 | 1.2 | 1.4 | 1.6 | 1.8 | 1.9 | 2.0 | 2.1 | 2.1 | 2.1 | 2.0 | 1.9 | 1.8 | 1.7 | 1.6 | 1.5 |
| | 1.91-1.95 | 1.0 | 1.2 | 1.4 | 1.7 | 1.9 | 2.0 | 2.1 | 2.1 | 2.1 | 2.1 | 2.0 | 1.9 | 1.8 | 1.7 | 1.6 | 1.6 |
| | 1.96-2.00 | 1.0 | 1.2 | 1.5 | 1.7 | 1.9 | 2.1 | 2.2 | 2.2 | 2.2 | 2.2 | 2.1 | 2.0 | 1.9 | 1.8 | 1.7 | 1.6 |
| | 2.01-2.05 | 1.0 | 1.3 | 1.5 | 1.7 | 1.9 | 2.1 | 2.2 | 2.3 | 2.3 | 2.2 | 2.1 | 2.0 | 1.9 | 1.8 | 1.7 | 1.6 |
| | 2.06-2.10 | 1.1 | 1.3 | 1.6 | 1.8 | 2.0 | 2.2 | 2.3 | 2.3 | 2.3 | 2.3 | 2.2 | 2.1 | 2.0 | 1.9 | 1.8 | 1.7 |
| | 2.11-2.15 | 1.1 | 1.3 | 1.6 | 1.8 | 2.0 | 2.2 | 2.4 | 2.4 | 2.4 | 2.3 | 2.2 | 2.1 | 2.0 | 1.9 | 1.8 | 1.7 |
| | 2.16-2.20 | 1.1 | 1.4 | 1.6 | 1.9 | 2.1 | 2.3 | 2.4 | 2.4 | 2.4 | 2.4 | 2.3 | 2.2 | 2.1 | 1.9 | 1.8 | 1.8 |
| | 2.21-2.25 | 1.1 | 1.4 | 1.7 | 1.9 | 2.1 | 2.3 | 2.4 | 2.5 | 2.5 | 2.4 | 2.3 | 2.2 | 2.1 | 2.0 | 1.9 | 1.8 |
| | 2.26-2.30 | 1.2 | 1.4 | 1.7 | 2.0 | 2.2 | 2.4 | 2.5 | 2.5 | 2.5 | 2.5 | 2.4 | 2.3 | 2.2 | 2.0 | 1.9 | 1.8 |
| | 2.31-2.35 | 1.2 | 1.5 | 1.7 | 2.0 | 2.2 | 2.4 | 2.5 | 2.6 | 2.6 | 2.5 | 2.5 | 2.3 | 2.2 | 2.1 | 2.0 | 1.9 |
| | 2.36-2.40 | 1.2 | 1.5 | 1.8 | 2.0 | 2.3 | 2.5 | 2.6 | 2.6 | 2.6 | 2.6 | 2.5 | 2.4 | 2.3 | 2.1 | 2.0 | 1.9 |
| | 2.41-2.45 | 1.2 | 1.5 | 1.8 | 2.1 | 2.3 | 2.5 | 2.6 | 2.7 | 2.7 | 2.6 | 2.6 | 2.4 | 2.3 | 2.2 | 2.0 | 1.9 |
| | 2.46-2.50 | 1.3 | 1.5 | 1.8 | 2.1 | 2.4 | 2.6 | 2.7 | 2.8 | 2.8 | 2.7 | 2.6 | 2.5 | 2.4 | 2.2 | 2.1 | 2.0 |

TABLE 4

11-15% break through
Adminstered Dose Calculator (GBq)
11-15% Lung Break-Through

| | | Percentage Tumour Involvement | | | | | | | | | | | | | | | |
|---|---|---|---|---|---|---|---|---|---|---|---|---|---|---|---|---|---|
| | | 0-5 | 6-10 | 11-15 | 16-20 | 21-25 | 26-30 | 31-35 | 36-40 | 41-45 | 46-50 | 51-55 | 56-60 | 61-65 | 66-70 | 71-75 | 76-80 |
| BSA | 1.30-1.35 | 0.7 | 0.8 | 1.0 | 1.2 | 1.3 | 1.4 | 1.5 | 1.5 | 1.5 | 1.5 | 1.4 | 1.3 | 1.3 | 1.2 | 1.1 | 1.1 |
| | 1.36-1.40 | 0.7 | 0.9 | 1.0 | 1.2 | 1.3 | 1.4 | 1.5 | 1.5 | 1.5 | 1.5 | 1.5 | 1.4 | 1.3 | 1.2 | 1.2 | 1.1 |
| | 1.41-1.45 | 0.7 | 0.9 | 1.1 | 1.2 | 1.4 | 1.5 | 1.6 | 1.6 | 1.6 | 1.6 | 1.5 | 1.4 | 1.4 | 1.3 | 1.2 | 1.2 |
| | 1.46-1.50 | 0.8 | 0.9 | 1.1 | 1.3 | 1.4 | 1.5 | 1.6 | 1.7 | 1.7 | 1.6 | 1.6 | 1.5 | 1.4 | 1.3 | 1.3 | 1.2 |
| | 1.51-1.55 | 0.8 | 1.0 | 1.1 | 1.3 | 1.5 | 1.6 | 1.7 | 1.7 | 1.7 | 1.7 | 1.6 | 1.5 | 1.5 | 1.4 | 1.3 | 1.2 |
| | 1.56-1.60 | 0.8 | 1.0 | 1.2 | 1.4 | 1.5 | 1.6 | 1.7 | 1.8 | 1.8 | 1.7 | 1.7 | 1.6 | 1.5 | 1.4 | 1.3 | 1.3 |
| | 1.61-1.65 | 0.8 | 1.0 | 1.2 | 1.4 | 1.6 | 1.7 | 1.8 | 1.8 | 1.8 | 1.8 | 1.7 | 1.6 | 1.6 | 1.5 | 1.4 | 1.3 |
| | 1.66-1.70 | 0.9 | 1.1 | 1.3 | 1.4 | 1.6 | 1.7 | 1.8 | 1.9 | 1.9 | 1.8 | 1.8 | 1.7 | 1.6 | 1.5 | 1.4 | 1.4 |
| | 1.71-1.75 | 0.9 | 1.1 | 1.3 | 1.5 | 1.7 | 1.8 | 1.9 | 1.9 | 1.9 | 1.9 | 1.8 | 1.7 | 1.6 | 1.5 | 1.5 | 1.4 |
| | 1.76-1.80 | 0.9 | 1.1 | 1.3 | 1.5 | 1.7 | 1.8 | 1.9 | 2.0 | 2.0 | 1.9 | 1.9 | 1.8 | 1.7 | 1.6 | 1.5 | 1.4 |
| | 1.81-1.85 | 0.9 | 1.1 | 1.4 | 1.6 | 1.8 | 1.9 | 2.0 | 2.0 | 2.0 | 2.0 | 1.9 | 1.8 | 1.7 | 1.6 | 1.5 | 1.5 |
| | 1.86-1.90 | 1.0 | 1.2 | 1.4 | 1.6 | 1.8 | 1.9 | 2.0 | 2.0 | 2.0 | 2.0 | 2.0 | 1.9 | 1.8 | 1.7 | 1.6 | 1.5 |
| | 1.91-1.95 | 1.0 | 1.2 | 1.4 | 1.7 | 1.9 | 2.0 | 2.0 | 2.0 | 2.0 | 2.0 | 2.0 | 1.9 | 1.8 | 1.7 | 1.6 | 1.6 |
| | 1.96-2.00 | 1.0 | 1.2 | 1.5 | 1.7 | 1.9 | 2.0 | 2.0 | 2.0 | 2.0 | 2.0 | 2.0 | 2.0 | 1.9 | 1.8 | 1.7 | 1.6 |
| | 2.01-2.05 | 1.0 | 1.3 | 1.5 | 1.7 | 1.9 | 2.0 | 2.0 | 2.0 | 2.0 | 2.0 | 2.0 | 2.0 | 1.9 | 1.8 | 1.7 | 1.6 |
| | 2.06-2.10 | 1.1 | 1.3 | 1.6 | 1.8 | 2.0 | 2.0 | 2.0 | 2.0 | 2.0 | 2.0 | 2.0 | 2.0 | 2.0 | 1.9 | 1.8 | 1.7 |
| | 2.11-2.15 | 1.1 | 1.3 | 1.6 | 1.8 | 2.0 | 2.0 | 2.0 | 2.0 | 2.0 | 2.0 | 2.0 | 2.0 | 2.0 | 1.9 | 1.8 | 1.7 |
| | 2.16-2.20 | 1.1 | 1.4 | 1.6 | 1.9 | 2.0 | 2.0 | 2.0 | 2.0 | 2.0 | 2.0 | 2.0 | 2.0 | 2.0 | 1.9 | 1.8 | 1.8 |
| | 2.21-2.25 | 1.1 | 1.4 | 1.7 | 1.9 | 2.0 | 2.0 | 2.0 | 2.0 | 2.0 | 2.0 | 2.0 | 2.0 | 2.0 | 2.0 | 1.9 | 1.8 |
| | 2.26-2.30 | 1.2 | 1.4 | 1.7 | 2.0 | 2.0 | 2.0 | 2.0 | 2.0 | 2.0 | 2.0 | 2.0 | 2.0 | 2.0 | 2.0 | 1.9 | 1.8 |
| | 2.31-2.35 | 1.2 | 1.5 | 1.7 | 2.0 | 2.0 | 2.0 | 2.0 | 2.0 | 2.0 | 2.0 | 2.0 | 2.0 | 2.0 | 2.0 | 2.0 | 1.9 |
| | 2.36-2.40 | 1.2 | 1.5 | 1.8 | 2.0 | 2.0 | 2.0 | 2.0 | 2.0 | 2.0 | 2.0 | 2.0 | 2.0 | 2.0 | 2.0 | 2.0 | 1.9 |
| | 2.41-2.45 | 1.2 | 1.5 | 1.8 | 2.0 | 2.0 | 2.0 | 2.0 | 2.0 | 2.0 | 2.0 | 2.0 | 2.0 | 2.0 | 2.0 | 2.0 | 1.9 |
| | 2.46-2.50 | 1.3 | 1.5 | 1.8 | 2.0 | 2.0 | 2.0 | 2.0 | 2.0 | 2.0 | 2.0 | 2.0 | 2.0 | 2.0 | 2.0 | 2.0 | 2.0 |

TABLE 5

16-20% break through
Adminstered Dose Calculator (GBq)
16-20% Lung Break-Through

| | | Percentage Tumour Involvement | | | | | | | | | | | | | | | |
|---|---|---|---|---|---|---|---|---|---|---|---|---|---|---|---|---|---|
| | | 0-5 | 6-10 | 11-15 | 16-20 | 21-25 | 26-30 | 31-35 | 36-40 | 41-45 | 46-50 | 51-55 | 56-60 | 61-65 | 66-70 | 71-75 | 76-80 |
| BSA | 1.30-1.35 | 0.7 | 0.8 | 1.0 | 1.2 | 1.3 | 1.4 | 1.5 | 1.5 | 1.5 | 1.5 | 1.4 | 1.3 | 1.3 | 1.2 | 1.1 | 1.1 |
| | 1.36-1.40 | 0.7 | 0.9 | 1.0 | 1.2 | 1.3 | 1.4 | 1.5 | 1.5 | 1.5 | 1.5 | 1.5 | 1.4 | 1.3 | 1.2 | 1.2 | 1.1 |
| | 1.41-1.45 | 0.7 | 0.9 | 1.1 | 1.2 | 1.4 | 1.5 | 1.5 | 1.5 | 1.5 | 1.5 | 1.5 | 1.4 | 1.4 | 1.3 | 1.2 | 1.2 |
| | 1.46-1.50 | 0.8 | 0.9 | 1.1 | 1.3 | 1.4 | 1.5 | 1.5 | 1.5 | 1.5 | 1.5 | 1.5 | 1.5 | 1.4 | 1.3 | 1.3 | 1.2 |
| | 1.51-1.55 | 0.8 | 1.0 | 1.1 | 1.3 | 1.5 | 1.5 | 1.5 | 1.5 | 1.5 | 1.5 | 1.5 | 1.5 | 1.5 | 1.4 | 1.3 | 1.2 |
| | 1.56-1.60 | 0.8 | 1.0 | 1.2 | 1.4 | 1.5 | 1.5 | 1.5 | 1.5 | 1.5 | 1.5 | 1.5 | 1.5 | 1.5 | 1.4 | 1.3 | 1.3 |
| | 1.61-1.65 | 0.8 | 1.0 | 1.2 | 1.4 | 1.5 | 1.5 | 1.5 | 1.5 | 1.5 | 1.5 | 1.5 | 1.5 | 1.5 | 1.5 | 1.4 | 1.3 |
| | 1.66-1.70 | 0.9 | 1.1 | 1.3 | 1.4 | 1.5 | 1.5 | 1.5 | 1.5 | 1.5 | 1.5 | 1.5 | 1.5 | 1.5 | 1.5 | 1.4 | 1.4 |
| | 1.71-1.75 | 0.9 | 1.1 | 1.3 | 1.5 | 1.5 | 1.5 | 1.5 | 1.5 | 1.5 | 1.5 | 1.5 | 1.5 | 1.5 | 1.5 | 1.5 | 1.4 |
| | 1.76-1.80 | 0.9 | 1.1 | 1.3 | 1.5 | 1.5 | 1.5 | 1.5 | 1.5 | 1.5 | 1.5 | 1.5 | 1.5 | 1.5 | 1.5 | 1.5 | 1.4 |
| | 1.81-1.85 | 0.9 | 1.1 | 1.4 | 1.5 | 1.5 | 1.5 | 1.5 | 1.5 | 1.5 | 1.5 | 1.5 | 1.5 | 1.5 | 1.5 | 1.5 | 1.5 |
| | 1.86-1.90 | 1.0 | 1.2 | 1.4 | 1.5 | 1.5 | 1.5 | 1.5 | 1.5 | 1.5 | 1.5 | 1.5 | 1.5 | 1.5 | 1.5 | 1.5 | 1.5 |
| | 1.91-1.95 | 1.0 | 1.2 | 1.4 | 1.5 | 1.5 | 1.5 | 1.5 | 1.5 | 1.5 | 1.5 | 1.5 | 1.5 | 1.5 | 1.5 | 1.5 | 1.5 |
| | 1.96-2.00 | 1.0 | 1.2 | 1.5 | 1.5 | 1.5 | 1.5 | 1.5 | 1.5 | 1.5 | 1.5 | 1.5 | 1.5 | 1.5 | 1.5 | 1.5 | 1.5 |
| | 2.01-2.05 | 1.0 | 1.3 | 1.5 | 1.5 | 1.5 | 1.5 | 1.5 | 1.5 | 1.5 | 1.5 | 1.5 | 1.5 | 1.5 | 1.5 | 1.5 | 1.5 |
| | 2.06-2.10 | 1.1 | 1.3 | 1.5 | 1.5 | 1.5 | 1.5 | 1.5 | 1.5 | 1.5 | 1.5 | 1.5 | 1.5 | 1.5 | 1.5 | 1.5 | 1.5 |
| | 2.11-2.15 | 1.1 | 1.3 | 1.5 | 1.5 | 1.5 | 1.5 | 1.5 | 1.5 | 1.5 | 1.5 | 1.5 | 1.5 | 1.5 | 1.5 | 1.5 | 1.5 |
| | 2.16-2.20 | 1.1 | 1.4 | 1.5 | 1.5 | 1.5 | 1.5 | 1.5 | 1.5 | 1.5 | 1.5 | 1.5 | 1.5 | 1.5 | 1.5 | 1.5 | 1.5 |
| | 2.21-2.25 | 1.1 | 1.4 | 1.5 | 1.5 | 1.5 | 1.5 | 1.5 | 1.5 | 1.5 | 1.5 | 1.5 | 1.5 | 1.5 | 1.5 | 1.5 | 1.5 |
| | 2.26-2.30 | 1.2 | 1.4 | 1.5 | 1.5 | 1.5 | 1.5 | 1.5 | 1.5 | 1.5 | 1.5 | 1.5 | 1.5 | 1.5 | 1.5 | 1.5 | 1.5 |
| | 2.31-2.35 | 1.2 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 |
| | 2.36-2.40 | 1.2 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 |
| | 2.41-2.45 | 1.2 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 |
| | 2.46-2.50 | 1.3 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 |

Administration of SIR-Spheres™ microspheres: SIR-Spheres™ microspheres were implanted on the third or fourth day of the first week of the first chemotherapy cycle. If implantation in the $1^{st}$ cycle was not possible, implantation on day 3 or 4 of the $2^{nd}$ cycle was allowed.

If the implantation was performed in cycle 2, oxaliplatin was given at a full dose in cycle 1 and the dose reduction in oxaliplatin took place in the cycle of implantation of SIR-Spheres™ microspheres. Re-escalation to full dose of oxaliplatin and introduction of bevacizumab, if applicable, was postponed until 6 weeks after the implantation.

Ancillary protocol treatment: in some instances a prophylactic $H_2$ blocking agent or proton pump inhibitor (e.g. ranitidine, omeprazole) needed to be administered to patients receiving SIRT for a minimum period of four weeks, commencing either just prior to or at the time of administration of SIR-Spheres™ microspheres. This was recorded as concomitant medication. Prophylactic narcotic analgesia was also administered in conjunction with SIRT as per standard hospital policy. Although minor opiates analgesia (e.g. codeine, dihydrocodeine) was usually sufficient, major opiates (e.g. pethidine) was occassionally required within the first 24 hours after SIRT.

All supportive treatment should be recorded, including any supportive treatment provided for the implantation of SIR-Spheres™ microspheres.

Alternate Protocol Treatment:

Patients were treated on day one with a 2-hour infusion of oxaliplatin at a dose of 60 mg/m2 and a 2-hour infusion of leucovorin at a dose of 200 mg/m². This treatment was then followed by delivery of a bolus of 5-fluorouracil at a dose of 400 mg/m² and then a 46-hour infusion of 5-fluorouracil at a dose of 2.4 g/m². At the conclusion of the 46-hour infusion of 5-fluorouracil patients received SIRT according to the following methodology. Chemotherapy cycles were repeated at two weekly intervals and continued for three cycles. SIRT was terminated after the first cycle.

Two weeks after completion of the third treatment cycle patients were treated with a 2-hour infusion of oxaliplatin at a dose of 85 mg/m² and a 2-hour infusion of leucovorin at a dose of 200 mg/m². This treatment was then followed by delivery of a bolus of 5-fluorouracil at a dose of 400 mg/m² and then a 46-hour infusion of 5-fluorouracil at a dose of 2.4 g/m².

Patients received a single dose of SIR-Spheres® microspheres that was administered on either the day third or fourth day of the first cycle of chemotherapy. The SIR-Spheres® microspheres were administered into the hepatic artery via a trans-femoral catheter that was placed using local anaesthetic. In patients where there was more than one hepatic artery supplying blood to the liver, the catheter was repositioned during administration and the total dose of SIR-Spheres® microspheres was divided into separate aliquots depending on the estimated volume of tumour being supplied by each feeding artery. Patients treated with SIR-Spheres® were generally kept in hospital overnight and discharged home the following day.

Patients were treated with a dose of SIR-Spheres microspheres that was calculated from the patient's body surface area and the size of the tumour within the liver according to using known dosimetry methods as described above.

Patient Responses

Patients were followed after trial entry with three monthly clinical evaluations and quality of life assessment (QoL), three-monthly CT scans of the abdomen were also carried out as were either a plain X-ray or CT scan of the chest. Further, regular monthly serologic tests of haematologic, liver and renal function and CEA were taken. Patients found to have obtained a complete (CR) or partial (PR) response on CT scan had a second confirmatory CT scan at not less than 4 weeks after the initial scan that showed the response.

Recording of Response and Toxicity: Response was determined using RECIST criteria (Therasse P et al (2000) *J Natl Cancer Inst* 92, 205-216). The RECIST criteria were developed with particular application for reporting the results of phase 2 trials and result in response outcomes that are very similar to those using the conventional WHO method.

Bevacizumab Administration

In all protocols used the dose of bevacizumab administered in the study was according to standard institutional protocols (usually 5-10 mg/kg) and was infused on the first day of each chemotherapy cycle, commencing with cycle 1 in the control arm. In the intervention arm, bevacizumab was withheld until at least cycle 4 to mitigate the risk of additive toxicity should the non-targeted delivery of SIR-Spheres® microspheres to the gastrointestinal tract occur. If non-targeted delivery was suspected, then a gastroduodenoscopy was undertaken before the initiation of bevacizumab therapy. If gastroduodenoscopy revealed an ulcer with biopsy-proven microspheres present, bevacizumab was withheld until resolution of the ulcer.

Non-Protocol Treatment: Once protocol treatment ceased, further cancer specific treatment, including non-protocol chemotherapy, was allowed to best manage patient care. All non-protocol cancer specific treatment was recorded in all patients. Other supportive, but not cancer specific treatment was allowed for patient management.

Outcome:

125 consecutive patients were randomised into the SIR-FLOX study. This number was selected so as to meet the criteria for 60 treated patients within each arm of the study.

The median progression free survival for patients on Chemotherapy plus bevacizumab alone was approximately 9.4 months. Those on the combination Chemotherapy plus SIRT Therapy had a median survival of approximately 12.5 months. This translates to a progression-free survival hazard ratio equal to 0.75.

The claims defining the invention are as follows:

1. A method for treatment of a cancer patient in need of treatment, which comprises the steps of:
   (i) delivering to said patient a treatment that lowers toxicity resulting from combining a radio-sensitizing agent oxaliplatin (OXA) with selective internal radiation therapy (SIRT), comprising on day one of a first chemotherapy treatment regime, comprising:
      (a) a 2-hour infusion of oxaliplatin (OXA) at a dose of about 60 to 80 mg/m$^2$;
      (b) a 2-hour infusion of leucovorin (LV) at a dose of about 100 to 400 mg/m$^2$;
      (c) followed by a bolus of 5-fluorouracil (5-FU) at a dose of about 300 to 500 mg/m$^2$ and then an infusion of 5-FU for about 40 to 50 hours at a dose of about 2.0 to 2.6 g/m$^2$; and repeating step (i), if required, then
   (ii) delivering selective internal radiation therapy (SIRT) to said patient between days 3 to 14 following either the commencement of step (i) or following the repeat of step (i);
   (iii) repeating step (i) for three cycles at an interval of one to three weeks between treatment cycles; then
   (iv) two weeks after the final treatment delivered in step (iii) delivering to said patient a second chemotherapy treatment regime, comprising:
      (a) a 2-hour infusion of OXA at a dose of about 85 to 100 mg/m$^2$;
      (b) a 2-hour infusion of LV at a dose of about 100 and 400 mg/m$^2$;
      (c) followed by a bolus of 5-FU at a dose of about 300 to 500 mg/m$^2$ and then an infusion of 5-FU for about 40 to 50 hours at a dose of about 2.0 to 2.6 g/m$^2$.

2. A method according to claim 1 further comprising the step of repeating step (iv) every 2 to 3 weeks, until the cancer is treated.

3. A method according to claim 1, wherein the dose of OXA used in step (i)(a) is selected from one of the following OXA doses: 60, 61, 62, 63, 64, 65, 66, 67, 68, 69, 70, 71, 72, 73, 74, 75, 76, 77, 78, 79, 80 mg/m$^2$.

4. A method according to claim 1, wherein the dose of OXA used in step (iv)(a) is selected from one of the following OXA doses: 85, 86, 87, 88, 89, 90, 91, 92, 93, 94, 95, 96, 97, 98, 99, 100 mg/m$^2$.

5. A method according to claim 1, wherein the dose of LV used in step (i)(b) or (iv)(b) is selected from one of the following LV doses: 100, 110, 120, 130, 140, 150, 160, 170, 180 and 190, 200, 210, 220, 230, 240, 250, 260, 270, 280, 290, 300, 310, 320, 330, 340, 350, 360, 370, 380, 390, 400 mg/m$^2$.

6. A method according to claim 1, wherein the bolus dose of 5-FU used in step (i)(c) or (iv)(c) is selected from one of the following 5-FU doses: 300, 310, 320, 330, 340, 350, 360, 370, 380, 390, 400, 410, 420, 430, 440, 450, 460, 470, 480, 490, 500 mg/m$^2$.

7. A method according to claim 1, wherein the infusion dose of 5-FU used in step (i)(c) or (iv)(c) is selected from one of the following 5-FU doses: 2.1, 2.2, 2.3, 2.4 and 2.5 g/m$^2$.

8. A method according to claim 1, comprising the step of treating the patient with bevacizumab.

9. A method according to claim 8 wherein bevacizumab is administered at a dose of about 5 to 10 mg/kg.

10. A method according to claim 9 wherein the bevacizumab is delivered to a patient in 30 to 60 minutes.

11. A method according to claim 8 wherein the bevacizumab therapy is delivered to said patient in the last cycle of therapy immediately after OXA therapy.

12. A method according to claim 1, wherein one or more chemotherapeutic agents additional to those used in the method are incorporated into systemic chemotherapy procedure drugs.

13. A method according claim 12 wherein the chemotherapeutic agents are selected from irinotecan or capecitabine.

14. A method according to claim 1, wherein the patient is also treated with an anti-angiogenesis factor.

15. A method according to claim 1, wherein the patient receives an amount of SIRT therapy suitable to effectively treat a cancer.

16. A method according to claim 1, wherein the SIRT therapy is administered using SIR-Spheres™ microspheres.

17. A method according claim 16 wherein the prescribed activity of the SIR-Spheres™ microspheres in both lobes of the liver is between 1.2 and 2.4 GBq.

18. The method according to claim 1, wherein step (iv) comprises two weeks after the final treatment is delivered in step (iii) a second chemotherapy treatment regime is delivered to said patient, wherein said second chemotherapy treatment regime comprises:
   (a) a 2-hour infusion of OXA at a dose of about 85 to 100 mg/m$^2$;
   (b) a 2-hour infusion of LV at a dose of about 100 and 400 mg/m$^2$;
   (c) followed by a bolus of 5-FU at a dose of about 300 to 500 mg/m$^2$ and a 15 to 90 minute infusion of bevacizumab at about 5 to 15 mg/kg, followed by an infusion of 5-FU for about 40 to 50 hours at a dose of about 2.0 to 2.6 g/m$^2$.

* * * * *